(12) United States Patent
Kimoto et al.

(10) Patent No.: US 7,316,647 B2
(45) Date of Patent: Jan. 8, 2008

(54) CAPSULE ENDOSCOPE AND A CAPSULE ENDOSCOPE SYSTEM

(75) Inventors: Seiichiro Kimoto, Tokyo (JP); Noriyuki Fujimori, Tokyo (JP); Hiroshi Suzushima, Tokyo (JP); Toshiaki Shigemori, Tokyo (JP); Tsutomu Nakamura, Tokyo (JP); Ayako Nagase, Tokyo (JP); Tetsuo Minai, Tokyo (JP); Hatsuo Shimizu, Tokyo (JP); Takemitsu Honda, Tokyo (JP); Katsuyoshi Sasagawa, Tokyo (JP); Katsuya Suzuki, Tokyo (JP); Masayuki Hashimoto, Tokyo (JP); Tatsuya Orihara, Tokyo (JP); Kazutaka Nakatsuchi, Tokyo (JP)

(73) Assignee: Olympus Corporation, Tokyo (JP)

( * ) Notice: Subject to any disclaimer, the term of this patent is extended or adjusted under 35 U.S.C. 154(b) by 408 days.

(21) Appl. No.: 10/830,846

(22) Filed: Apr. 23, 2004

(65) Prior Publication Data

US 2004/0225189 A1 Nov. 11, 2004

(30) Foreign Application Priority Data

Apr. 25, 2003 (JP) ............................. 2003-122807

(51) Int. Cl.
*A61B 1/06* (2006.01)
(52) U.S. Cl. .................... 600/179; 600/160; 600/178
(58) Field of Classification Search ................ 600/160, 600/178, 179
See application file for complete search history.

(56) References Cited

U.S. PATENT DOCUMENTS

| 6,227,679 | B1 | 5/2001 | Zhang et al. | |
| 6,502,956 | B1 | 1/2003 | Wu | |
| 6,569,088 | B2* | 5/2003 | Koshikawa | 600/177 |
| 6,855,111 | B2* | 2/2005 | Yokoi et al. | 600/179 |
| 2001/0003142 | A1 | 6/2001 | Koshikawa | |
| 2002/0198439 | A1 | 12/2002 | Mizuno | |
| 2003/0028078 | A1* | 2/2003 | Glukhovsky | 600/109 |
| 2003/0060734 | A1 | 3/2003 | Yokoi et al. | |
| 2003/0130562 | A1* | 7/2003 | Barbato et al. | 600/109 |
| 2006/0155174 | A1* | 7/2006 | Glukhovsky et al. | 600/301 |

FOREIGN PATENT DOCUMENTS

| JP | 2-104315 | 8/1990 |
| JP | 4-102432 | 4/1992 |
| JP | 5-60985 | 3/1993 |
| JP | 11-76151 | 3/1999 |
| JP | 2001-095756 | 4/2001 |
| JP | 2003-93367 | 4/2003 |
| JP | 2003-235796 | 8/2003 |
| WO | WO 01/35813 A1 | 5/2001 |

* cited by examiner

*Primary Examiner*—John P. Leubecker
(74) *Attorney, Agent, or Firm*—Scully, Scott, Murphy & Presser, P.C.

(57) ABSTRACT

In a capsule endoscope illuminating units are disposed around an image capturing unit in such a manner that an optical axis of the illuminating units do not intersect with an optical axis of the observation unit, and illumination areas of the illuminating units overlap at substantially a central portion of an image capturing area of the image capturing unit.

11 Claims, 6 Drawing Sheets

CAPSULE ENDOSCOPE AND A CAPSULE ENDOSCOPE SYSTEM

BACKGROUND OF THE INVENTION

1) Field of the Invention

The present invention relates to swallowable and capsule-shaped endoscopes and a capsule endoscope system.

2) Description of the Related Art

Swallowable and capsule-shaped endoscopes are known in the art. A patient swallows such a capsule endoscope and as the capsule endoscope passes through an abdominal cavity, it captures images of a stomach, intestines etc. An example of such a capsule endoscope is described below with reference to FIG. 9.

As shown in FIG. 9, the conventional capsule endoscope includes a watertight capsule casing 8 having a front cover 5. The capsule casing 8 houses an image capturing unit 1 that captures images of an inside the abdominal cavity, an illuminating unit 2 that outputs a light to illuminate the inside of the abdominal cavity, a power-supply unit 3 that supplies power to the image capturing unit 1 and the illuminating unit 2.

The illuminating unit 2 and the image capturing unit 1 are disposed near each other and they face toward a front side through the front cover 5. The front cover 5 is partly or fully transparent so that when the illuminating unit 2 outputs the light, the light illuminates the inside of the abdominal cavity and the image capturing unit 1 can capture images of inside of the abdominal cavity.

The front cover 5 is semispherical, because, it is easier for a patient to swallow the capsule endoscope if the front cover 5 is semispherical, and body fluids can not remain on the front cover 5 if the front cover 5 is semispherical (see Japanese Patent Application Laid-open Publication No. 2001-95756).

However, the illuminating unit 2 disclosed in Japanese Patent Application Laid-open Publication No. 2001-95756 has problems as explained below. As shown in FIG. 10, when many illuminating units 2 are arranged around the image capturing unit 1 on a circle, light from all the illuminating units 2 overlap at a portion that is in front of the image capturing unit 1 and the portion where the lights overlap is brighter that the portion where there is no overlap.

Because of the unbalance in the brightness, the image quality of the images captured by the image capturing unit degrades and good diagnosis becomes difficult.

SUMMARY OF THE INVENTION

It is an object of the present invention to solve at least the problems in the conventional technology.

A capsule endoscope according to an aspect of the present invention has an observation unit that has a predetermined observation range and that observes inside of a body of a patient; and a plurality of illuminating units that output light and illuminate the observation range of the observation unit with the light output, wherein each of the illuminating units have a light distribution characteristics that deviates from a center of the observation range of the observation unit, and the lights output by the illuminating units are made to overlap at substantially a central portion of the observation range of the observation unit such that an intensity of the light at the central portion of the observation range is substantially equally to an intensity at a portion other than the central portion of the observation range.

A capsule endoscope according to an aspect of the present invention has an image capturing unit having an optical axis and a vision range and that captures an image of an inside of a body of a patient; and a plurality of illuminating units that output light and illuminate the vision range of the image capturing unit with the light output, wherein each of the illuminating units have a light distribution characteristics that deviates from the optical axis of the image capturing unit, and the lights output by the illuminating units are made to overlap at substantially a central portion of an observation range that is on a line that is an extension of the optical axis of the image capturing unit such that an intensity of the light at the central portion of the observation range is substantially equally to an intensity at a portion other than the central portion of the observation range.

A capsule endoscope according to still another aspect of the present invention includes an image capturing unit that acquires an image of a image capturing portion; and a plurality of illuminating units arranged around the image capturing unit in such a manner that illumination areas of a predetermined number of the illuminating units overlap in such a manner that an intensity of the light in the image capturing portion becomes substantially uniform.

The other objects, features, and advantages of the present invention are specifically set forth in or will become apparent from the following detailed description of the invention when read in conjunction with the accompanying drawings.

DETAILED DESCRIPTION

Exemplary embodiments of a capsule endoscope and a capsule endoscope system according to the present invention are described below in detail with reference to the accompanying drawings.

Figure 1:
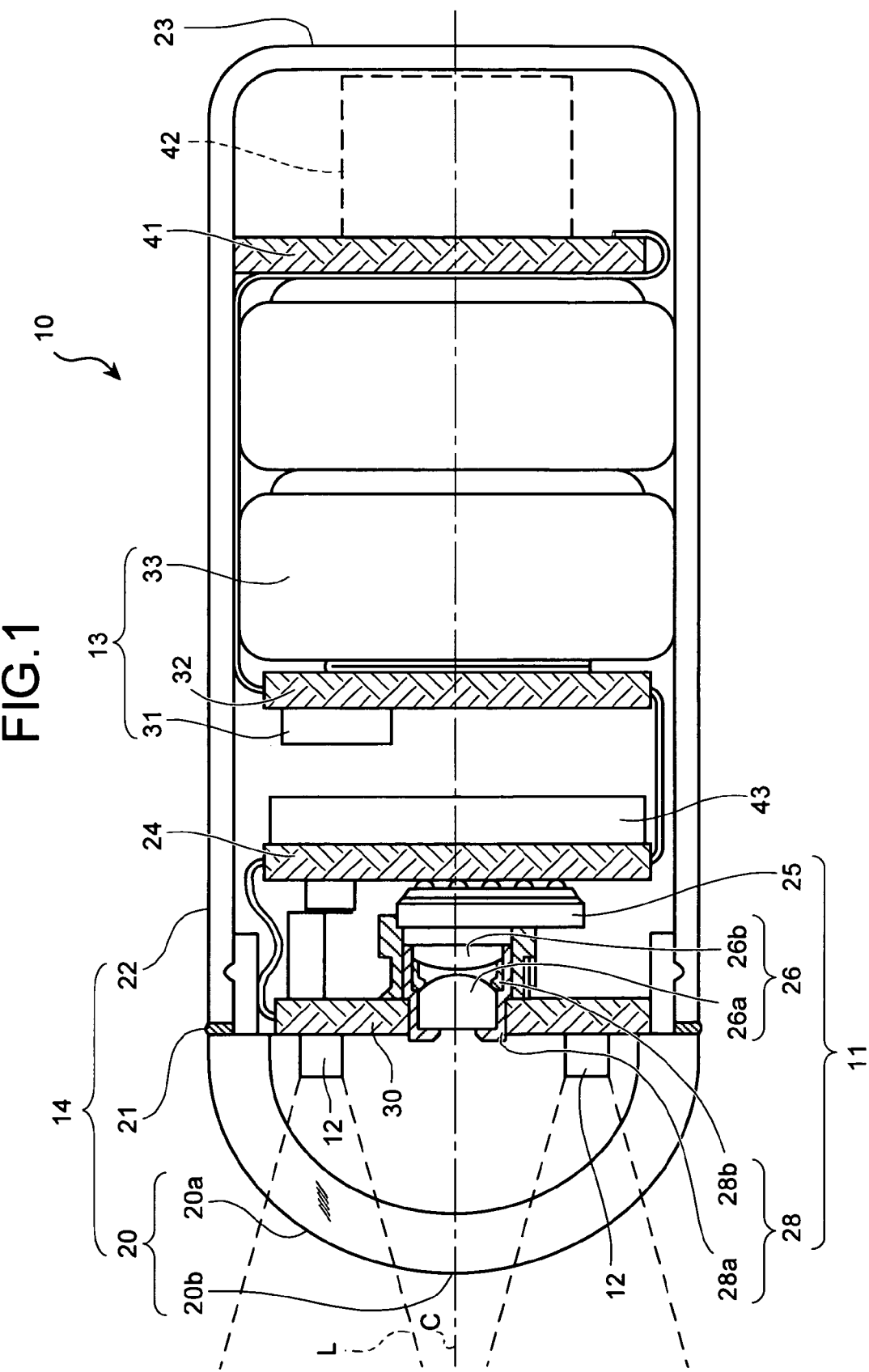
FIG. 1 is a schematic diagram of an internal structure of a capsule endoscope according to the present invention.
Figure 2:
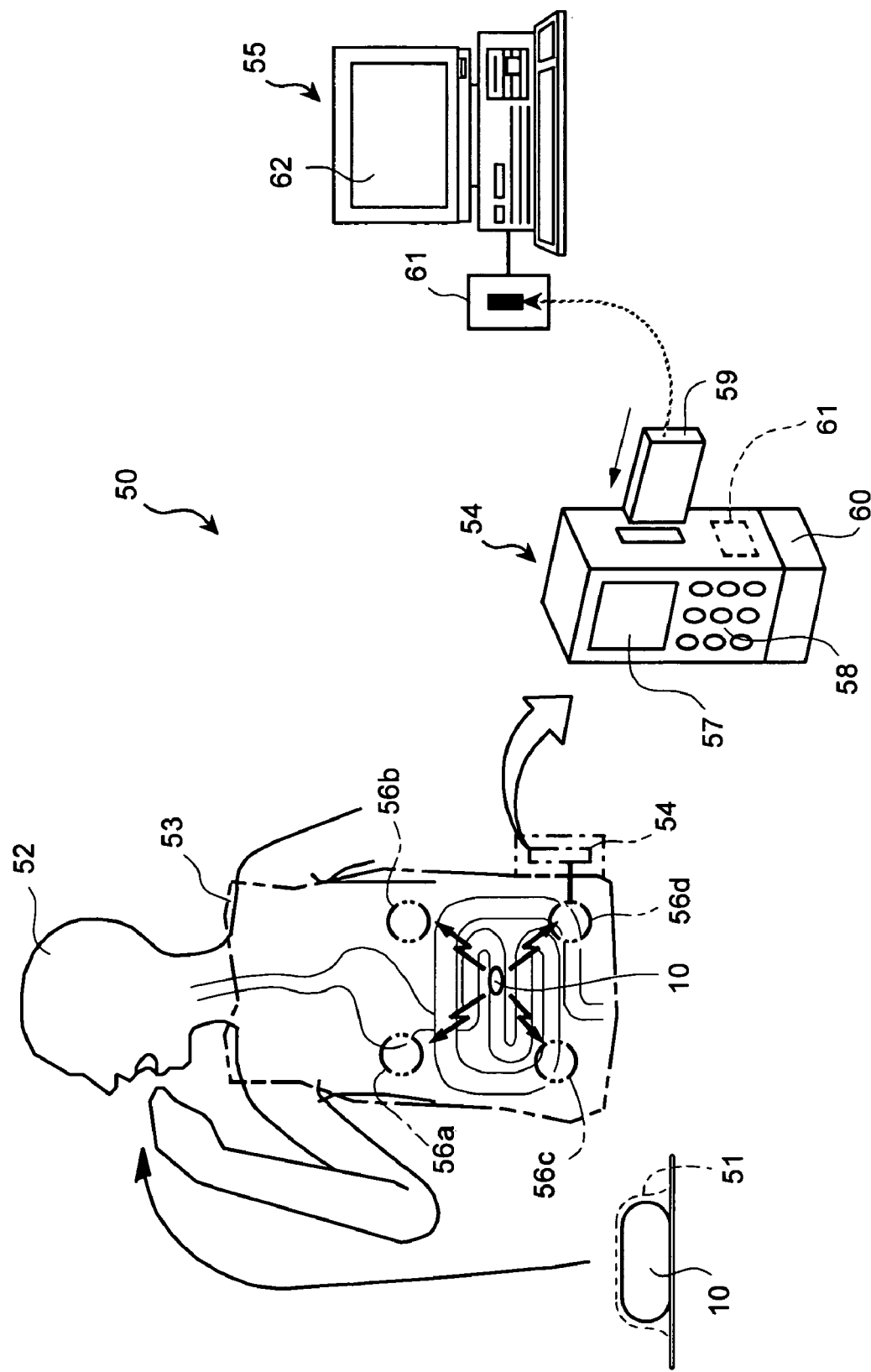
FIG. 2 is a schematic diagram of a capsule endoscope system.
Figure 3:
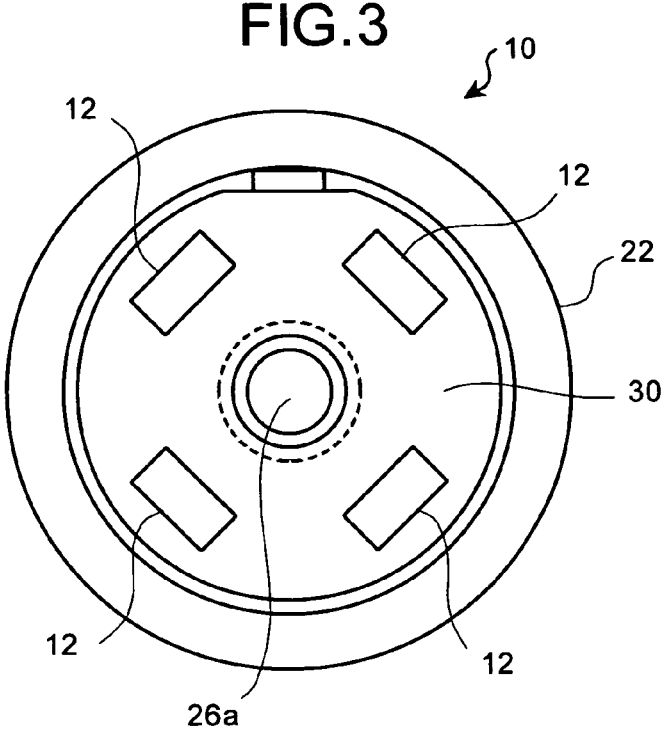
FIG. 3 is a front view of a capsule endoscope according to one embodiment.
Figure 4:
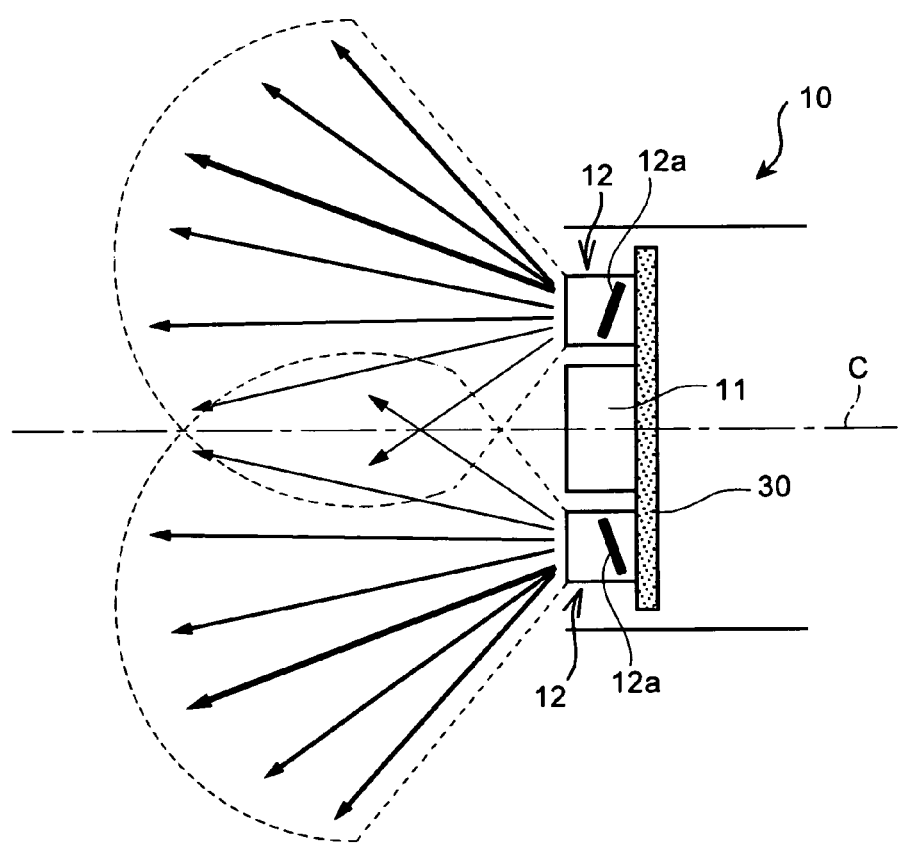
FIG. 4 is a schematic diagram for explaining emission of a light from an illuminating unit of the capsule endoscope shown in FIG. 3.
Figure 5:
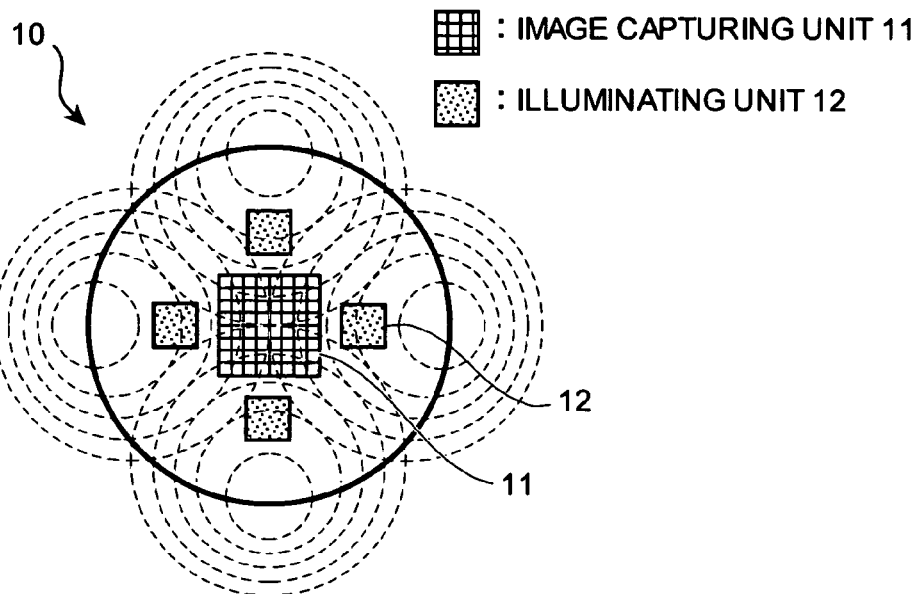
FIG. 5 is a schematic diagram to explain intensity of the light emitted from the illuminating unit of the capsule endoscope shown in FIG. 3.

FIG. 1 is a schematic diagram of an internal structure of a capsule endoscope according to the present invention; FIG. 2 is a schematic diagram of a capsule endoscope system; FIG. 3 is a front view of a capsule endoscope according to one embodiment; FIG. 4 is a schematic diagram for explaining emission of a light from an illuminating unit of the capsule endoscope shown in FIG. 3; FIG. 5 is a schematic diagram to explain intensity of the light emitted from the illuminating unit of the capsule endoscope shown in FIG. 3.

FIG. 1 is a schematic diagram of an internal structure of a capsule endoscope according to the present invention and FIG. 2 is a schematic diagram of a capsule endoscope system An overall internal structure of the capsule endoscope 10 is described by referring to FIG. 1. The capsule endoscope 10 includes a watertight capsule casing 14. The capsule casing 14 includes a capsule trunk 22 that houses an image capturing unit 11 that captures images of an inside of an abdominal cavity, an illuminating unit 12 that outputs a light to illuminate the inside of the abdominal cavity, a power-supply unit 13 that supplies an electric power to both the image capturing unit 11 and the illuminating unit 12.

The capsule casing 14 has a front cover 20 with a window 20a that allows the light L output from the illuminating unit 12 to pass through but does not allow a reflected light of the light L to reach to the image capturing unit 11. A rear cover 23, if required, may be provided to the capsule trunk 22. It is assumed that, the rear cover 23 is provided integrally with the capsule trunk and is flat, however, the rear cover may be dome-shaped.

The front cover 20 may be divided clearly into a window 20a for illumination that allows light L from the illuminating unit 12 to pass through and a window 20b for image capturing through which the image capturing unit captures the images. Further, in the present embodiment, the whole of the front cover 20 is transparent and areas of the window 20a and the window 20b are partly overlapping.

The image capturing unit 11 is installed on an image capturing substrate 24. The image capturing unit 11 includes a solid-state image sensor 25 and an image forming lens 26. The solid-state image sensor 25 is, for example, a charged couple device (CCD), and captures images in the range that is illuminated by the light L. The image forming lens 26 includes a fixed lens 26a which forms an image of an object on the solid-state image sensor 25 and a movable lens 26b. The image forming lens 26 forms a sharp image by being controlled by a focusing unit 28. The focusing unit 28 includes a fixing frame 28a to firmly hold the fix lens 26a and a movable frame 28b to movably hold the movable lens 26b.

The image capturing unit 11 is not limited to the CCD, but may be a complementary metal-oxide semiconductor (CMOS).

The illuminating unit 12 is provided on an illuminating substrate 30 is, for example, a light emitting diode (LED). A plurality of the illuminating units 12 (four in the present embodiment) are disposed around the image forming lens 26.

The power-supply unit 13 is installed on a power-supply substrate 32 that has an internal switch 31. A button battery cell (hereinafter, "button cell") 33, for example, is used as a source of the power supply. It is assumed here that the button cell is a silver-oxide cell; however, the button cell may be a rechargeable cell, a dynamo cell, and the like.

It is assumed here that the internal switch 31 is a magnetic switch that can be made ON/OFF using a magnet.

A wireless unit 42, which includes an antenna etc., for performing wireless communication with outside is installed on a wireless substrate 41 and performs communication with the outside according to the requirement.

A signal-processing and control unit 43 that processes and controls the various units mentioned above is installed on the image capturing substrate 24 and executes various processes in the capsule endoscope.

The signal-processing and control unit 43 includes an image-signal processing function of image-data generation etc. which includes correlated double sampling (CDS), for example, a transmission-signal generating function to perform mixing of an image signal and a synchronization signal (in a case of analog transmission) and addition of a mistake-correction sign (in a case of digital transmission), a modulation function to convert in cooperation with a modulator, to a phase-shift keying (PSK) modulation, a minimum-shift keying (MSK) modulation, a Gaussian minimum-shift keying (GMSK) modulation, a quadrature minimum-shift keying (QMSK) modulation, and an amplitude-shift keying (ASK) modulation format, for example, a power-supply control function to control the power supply according to ON-OFF operation of a switch, a timing-generator (TG) function to control a driver circuit like an LED driver circuit, a storage function to store various data like parameters of line and frame etc. and performs various signal processing and controls.

The signal processing may include image-data correction (white balance (WB) correction, γ correction, color processing, automatic gain control (AGC) etc.), analog-digital conversion (ADC), automatic exposure control function (AE), and the like.

FIG. 2 is a schematic diagram of the capsule endoscope system 50 according to the present embodiment. The capsule endoscope system 50 uses the capsule endoscope 10 to check a patient.

The capsule endoscope system 50 includes, for example, the capsule endoscope 10 and its package 51, a jacket 53 that is to be worn by a patient 52, a detachable receiver 54 that can be detachably attached to the jacket 53, and a work station 55 that processes information which is received in the receiver 54.

Antennas 56a, 56b, 56c, and 56d which catch electric waves of image signals transmitted from the wireless unit 42 of the capsule endoscope 10 are installed in the jacket 53 and are provided to enable wireless communication or wired communication by a cable with the receiver 54. Further, number of antennas installed in the jacket 53 is not limited to four and would be more so that the electric waves from the capsule endoscope 10 can be received properly.

The receiver 54 includes a display 57 that displays information necessary for observation (examination) and an input section 58 to input information necessary for observation (examination). Moreover, a CF (compact flash (registered trademark)) memory 59 that stores image data, is detachably mounted on the receiver 54. Further, the receiver 54 is provided with a power-supply unit 60 that can supply power even while carrying and a signal processing and control section 61 that performs processing required for observation (examination). A dry battery cell, a lithium-ion secondary battery cell, nickel-hydrogen battery cell etc. are examples of the power-supply unit 60 and it may be a rechargeable battery cell as well.

The work station 55 has processing functions to perform diagnosis based on images of internal organs in a body of a patient which a doctor or a nurse has captured by the capsule endoscope 10. This work station 55 is provided with a CF memory reader/writer 61. It is not shown in the diagram but the receiver 54 and the CF memory reader/writer 61 have interfaces that can be connected to enable communication, and read and write the CF memory 59.

Moreover, the work station 55 has a communication function for connecting to a network and via this network a medical examination result of the patient is stored in a database. Further, the work station 55 has a display 62 and inputs the captured image data of inside of the patient's body from the receiver 54 and displays images of internal organs etc. on the display 62.

When carrying out the examination, the capsule endoscope 10 is taken out from the package 51 and the patient 52 swallows the capsule endoscope 10. The capsule endoscope 10 passes through esophagus of the patient, advances to an abdominal cavity due to peristalsis of an alimentary canal cavity and captures images inside the abdominal cavity one after another.

The capsule endoscope 10 transmits, continuously or intermittently, the electric signals corresponding to the captured images via the wireless unit 42. The antennas 56a to 56d receive those electric signals and transmit them to the receiver 54.

The receiver 54 stores the electric signals in the CF memory 59 in the form of captured image data. The operation of the receiver 54 is not synchronized with the start of image capturing of the capsule endoscope 10, but, the start and the end of receiving are controlled by an operation of the input section 58. Moreover, the captured image data may be still-image data that is captured at a plurality of frames per second for displaying them as moving images or may be normal video-image data.

When the observation (examination) of the patient 52 by the capsule endoscope 10 is completed, the CF memory 59 is taken out of the receiver 54 and inserted into the CF memory reader/writer 61. The data in the CF memory 59 is transferred to the work station 55. In the work station 55, the data for each patient is stored and managed separately.

Thus, the captured image data of the inside of the abdominal cavity that is captured by the capsule endoscope 10 and stored by the receiver 54 is displayed as image data by the display 62 in the work station 55. This enables to acquire data useful for physiological research and to make a diagnosis of a physical change caused by a disease of the entire alimentary canal in the human body including internal organs which are not accessible (like a small intestine) by an ultrasonic probe, endoscope etc.

The illuminating unit according to the present embodiment is shown in FIGS. 3 and 4.

Each illuminating unit 12 includes a light emitting body 12a. Each light emitting body 12a is tilted outward from a central axis C of the capsule endoscope 20 and tilted from a front side towards a back side so that a center of axis of the light L from each the light emitting bodies 12a is inclined away from the central axis C. The central axis C passes through a center of an observation region, and it is also a center of the capsule trunk 22 of the capsule endoscope 10 shown in FIG. 1. It is assumed here that the optical axis of the image forming lens 26 of the image capturing unit 11 and the center axis C coincide; however, they need not coincide. If they do not coincide, the light emitting body 12a is tilted outward from the optical axis of the image forming lens 26 from a front side towards a back side so that the optical axis of the image forming lens 26 functions as the center of the observation region.

Because the light emitting bodies 12a in the illuminating units 12 are tilted in this manner, although there is an overlap of light in the central portion, the brightness at the central portion of the observation region and the portion other than the central portion of the observation region is substantially the same.

In other words, as shown in FIG. 5, when the illuminating units are disposed around the image capturing unit 11, when brightness of the light L from the illuminating unit 12 is indicated by constant-light lines (amount of light is maximum where distance between the lines is small), the intensity of the light is adjusted such that central light towards an outer side of the capsule endoscope rather than central side of the illuminating unit 12 is high and the light that illuminates the central portion of the illuminating range of the light that is emitted from the light emitting body 12a in the illuminating unit 12 is allowed to be incident in a different direction (hereinafter, "anisotropy factor of light") such that the brightness of the light that illuminates the observation central portion of the illuminating range of the light from the light that is emitted from the light emitting body 12a in the illuminating unit 12 is less than incident light that illuminates a portion excluding the illuminating range of the observation central portion of the illuminating range.

As a result, a brightness of the observation central portion of the illuminating range that is illuminated by the plurality of light emitting bodies 12a and the brightness of the portion excluding the observation central portion of the illuminating range that is illuminated by a single light emitting body becomes same or substantially same.

According to the present embodiment, since the observation central portion of the illuminating range has a predetermined brightness because of an overlap of lights from the plurality (four in the present embodiment) of the light emitting bodies 12a, 12a, 12a, and 12a and in the portion other than the observation central portion of the illuminating range has substantially the same brightness as the brightness of the central portion, with merely the light emitting body 12a, the overall illuminating range can be made to have a uniform brightness, thereby having balanced brightness. As a result, it is possible to provide the capsule endoscope that enables to capture a good diagnosis image with the image capturing unit.

Due to this, the amount of light of the light in a plane that is identical to a plane perpendicular to the central axis of the capsule endoscope is allowed to be roughly the same.

There is example drawback in the conventional capsule endoscope is that although the desired brightness can be acquired in the central portion, the desired brightness cannot be acquired in a portion other than the central portion.

If the power supply from the power-supply unit 13 is increased to obtain the desired brightness in a portion other than the central portion, then the central portion becomes brighter than desired, moreover, this also leads to increased power consumption.

For this, since by making an arrangement as in the present embodiment, the observation central portion of the illuminating range is allowed to acquire the desired brightness by using the plurality of light emitting sections and the portion excluding the central portion is allowed to acquire roughly the same or the same brightness as that of the central portion by using a single light emitting body, the central portion can acquire the desired brightness and an occurrence of a situation in which the portion other than the central portion cannot acquire the desired brightness can be avoided.

In other words, according to the present embodiment, in a case where the portion other than the central portion does not have the desired brightness, the central portion does not have the desired, brightness similarly. In such a case, when the power supply from the power-supply unit 13 is increased, the overall portion becomes bright. Therefore, the power supply can be used effectively and it is possible to prevent unnecessary power consumption as in the conventional case.

Figure 6:
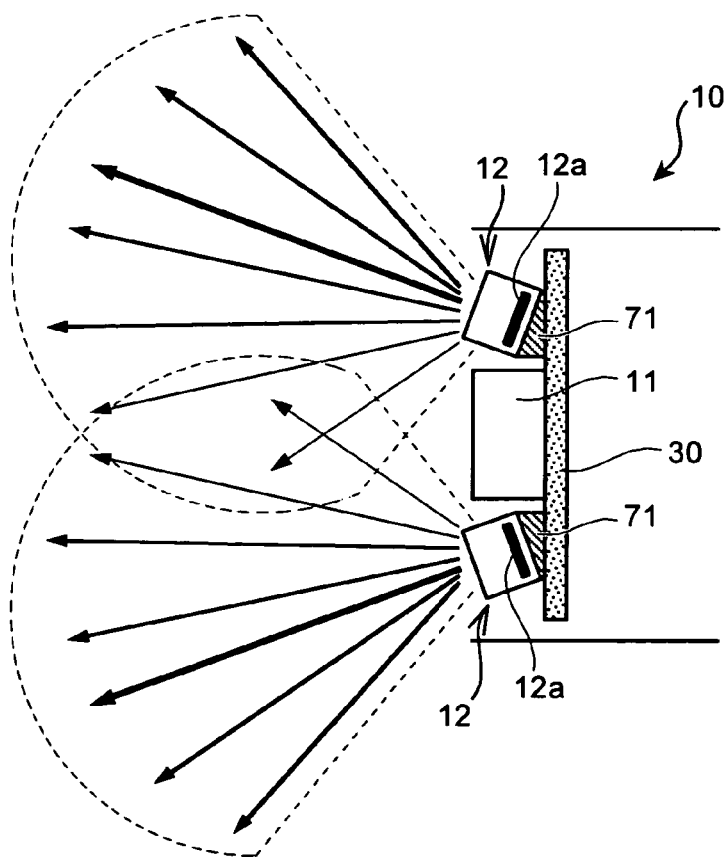
FIG. 6 is a schematic diagram for explaining emission of a light from an illuminating unit of a capsule endoscope according to a second embodiment.

FIG. 6 is a schematic diagram for explaining emission of a light from an illuminating unit of a capsule endoscope according to a second embodiment.

In the first embodiment shown in FIG. 4 the light emitting bodies 12*a* in the illuminating unit 12 are tilted. In the second embodiment, as shown in FIG. 6, the illuminating units 12 themselves are tilted by using a tilting member 71 such that the illuminating units 12 are inclined from front side towards back side in an outward direction from the central axis of the capsule endoscope.

A light emitting surface of the light emitting body 12*a* and a light emitting surface of the illuminating unit 12 are parallel. Therefore, there is no change incorporated in a structure of the illuminating unit 12. The existing illuminating units may be used and tilting is provided by the tilting member 71. By tilting, the observation central portion of the illuminating range is allowed to acquire a predetermined brightness due to the light gathered from the plurality of light emitting sections and the illuminating range other than the central portion is allowed to acquire roughly the same or the same brightness as the predetermined brightness of the central portion by using a single light emitting section 12*a*. Therefore, the overall illuminating range has a uniform brightness, thereby imparting balance of the brightness. As a result, it is possible to provide the capsule endoscope that enables to capture a good diagnosis image with the image capturing unit.

Figure 7:
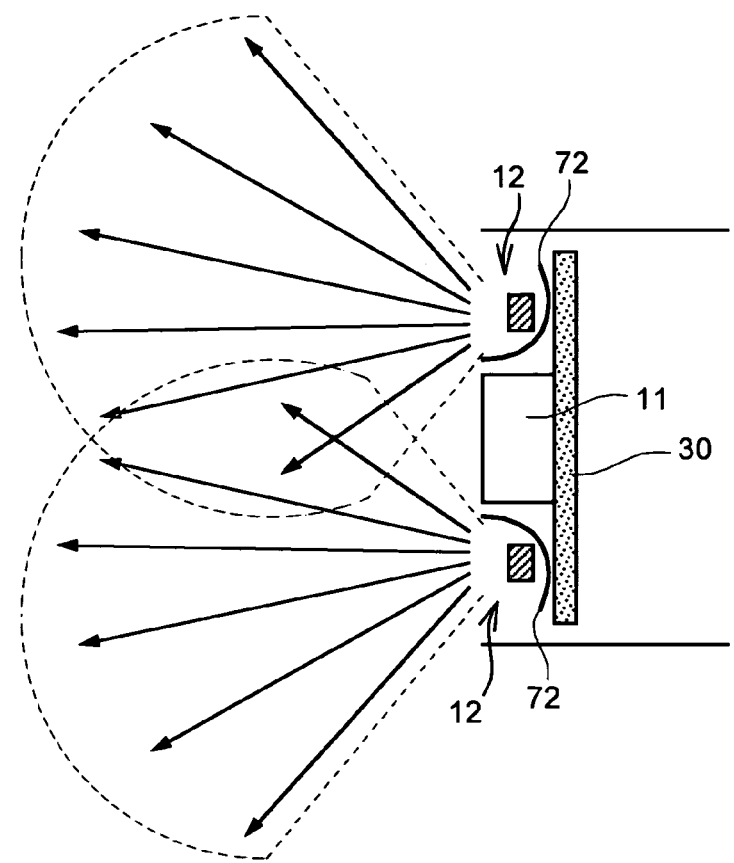
FIG. 7 is a schematic diagram for explaining emission of a light from an illuminating unit of a capsule endoscope according to a third embodiment.
Figure 8:
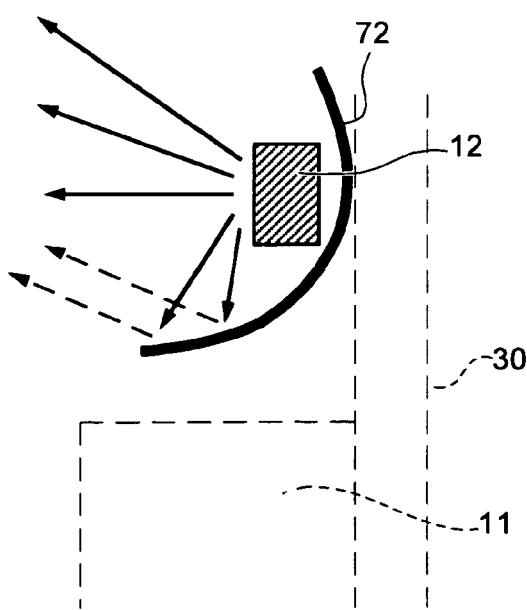
FIG. 8 is an enlarged view for explaining emission of a light from an illuminating unit of a capsule endoscope according to the third embodiment.
Figure 9:
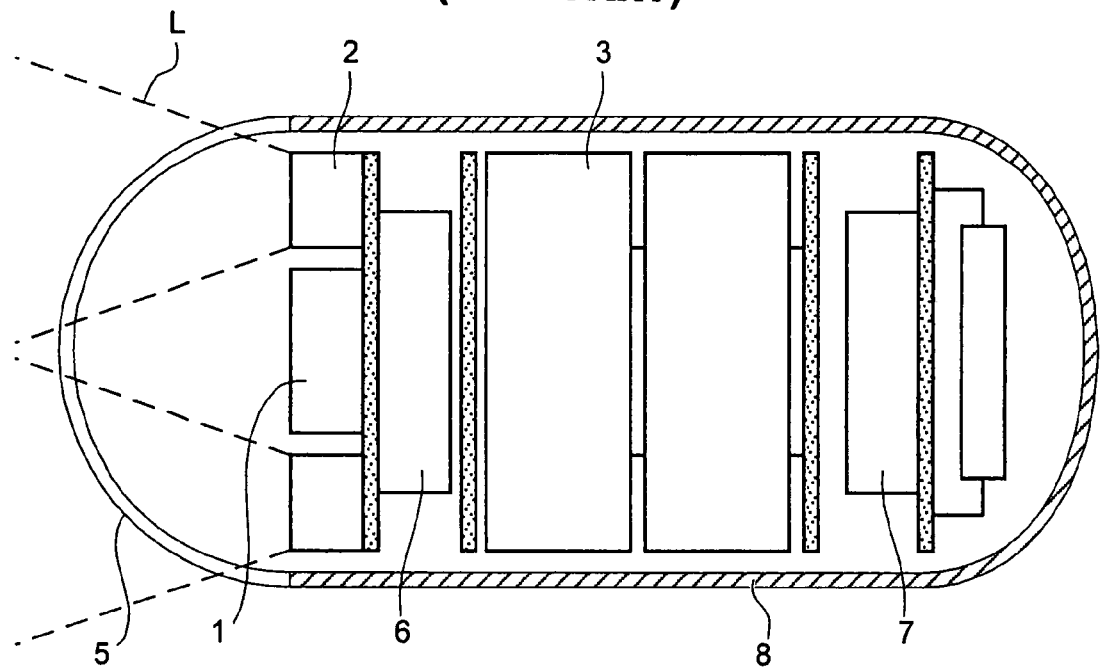
FIG. 9 is a schematic diagram of a conventional capsule endoscope.
Figure 10:
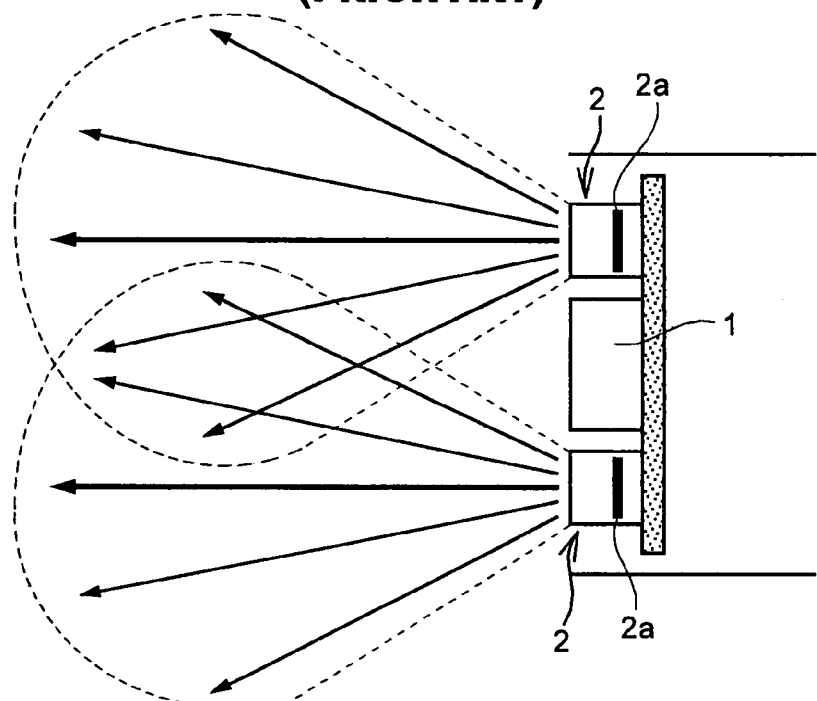
FIG. 10 is a schematic diagram for explaining emission of a light from an illuminating unit of the conventional capsule endoscope.

FIG. 7 is a schematic diagram for explaining emission of a light from an illuminating unit of a capsule endoscope according to a third embodiment. FIG. 8 is an enlarged view for explaining emission of a light from an illuminating unit of a capsule endoscope according to the third embodiment.

As shown in FIGS. 7 and 8, in the present embodiment, instead of tilting the illuminating unit 12 with an inbuilt light emitting body 12*a* by using the tilting member 71 as in the second embodiment, a reflecting member 72 is provided on a back side of the illuminating unit 12. A part of emitting light that is emitted from the illuminating unit 12 is caused to reflect from the reflecting member 72, thereby changing orientation characteristics. Thus, a total of the light including reflected light and emerged light is allowed to have an anisotropy factor of light.

According to the present embodiment, not only the emerged light but also a part of the emerged light is caused to be reflected by using the reflecting member 72 on the back surface of the illuminating unit 12. Therefore, there is not change incorporated in a structure of the illuminating unit 12. The existing illuminating unit is used and the light is a total of the emerged light and the reflected light. An observation central portion of the illuminating range is allowed to acquire a predetermined brightness by the light gathered from the plurality of light emitting sections and the illuminating range other than the central portion is allowed to acquire roughly the same or the same brightness as the predetermined brightness of the central portion by using a single light emitting body 12*a*. Therefore, the overall illuminating range has a uniform brightness, thereby imparting balance of the brightness. As a result, it is possible to provide the capsule endoscope that enables to capture a good diagnosis image with the image capturing unit.

Moreover, in the present embodiment, the image capturing unit 11 is disposed in the central portion and the illuminating units 12 are disposed around, and the number of the illuminating units 12 is not limited in particular.

Furthermore, in the present invention, the illuminating unit 12 is not to be disposed around the image capturing unit 11 restrictedly and any structure in which the plurality of illuminating units 12 is used to illuminate uniformly an image capturing range in the capsule endoscope can be used for the illuminating unit.

Thus, according to the present invention, it is possible to provide a capsule endoscope that enables to capture a good diagnosis image by allowing a uniform illumination of overall illuminating plane by light.

Moreover, since an illuminating range becomes uniform by using this capsule endoscope, a good image can be captured, and it is possible to provide a capsule endoscope system that enables to contribute to an improved diagnostic analysis.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. A capsule endoscope comprising:
an observation unit that has a predetermined observation range and that observes inside of a body of a patient;
a plurality of illuminating units that output light and illuminate the observation range of the observation unit with the light output;
a reflector that reflects at least a part of the light output from each illuminating unit in such a manner that
an optical axis of the light output by the illuminating unit and an optic axis of the light reflected incline in a direction that points away from an optical axis of the observation unit and also a front direction to a back direction, and
an illumination area of the illuminating unit and an illumination area of the reflector overlap the central portion of the observation range of the observation unit, wherein
each illuminating unit has a light distribution characteristic that deviates from a center of the observation range of the observation unit.

2. A capsule endoscope comprising:
an image capturing unit having an optical axis and a vision range, and capturing an image of an inside of a body of a patient; and
a plurality of illuminating units disposed around the image capturing unit, each illuminating unit including a light emitting body whose emitting surface is substantially parallel to an emitting surface of the corresponding illuminating unit, each illuminating unit outputting light and illuminating the vision range of the image capturing unit with the light output, wherein
each illuminating unit is disposed so that the emitting surface of the illuminating unit is inclined in an outward direction from the optical axis of the image capturing unit.

3. The capsule endoscope according to claim 2, further comprising a plurality of tilting members corresponding respectively to the illuminating units, wherein each illuminating unit is disposed on a substrate via the corresponding tilting member.

4. The capsule endoscope according to claim 3, wherein the illuminating units have a light distribution characteristic that uniformly illuminates the vision range of the image capturing unit.

5. The capsule endoscope according to claim 4, wherein illuminating ranges of the illuminating units overlap so that the vision range of the image capturing unit is uniformly illuminated.

6. The capsule endoscope according to claim 3, wherein
each illuminating unit has a bottom surface parallel to the emitting surface of the illuminating unit, and
each tilting member inclines the bottom surface of the corresponding illuminating unit against the substrate.

7. The capsule endoscope according to claim 2, wherein each illuminating unit is a light emitting diode.

8. The capsule endoscope according to claim 2, wherein each illuminating unit has a bottom surface substantially parallel to the emitting surface of the illuminating unit.

9. A capsule endoscope comprising:
an image capturing unit having an optical axis and a vision range, and capturing an image of an inside of a body of a patient;
a plurality of illuminating units disposed around the image capturing unit, each illuminating unit including a light emitting body whose emitting surface is substantially parallel to an emitting surface of the corresponding illuminating unit, each illuminating unit outputting light and illuminating the vision range of the image capturing unit with the light output; and
a plurality of tilting members corresponding respectively to the illuminating units, each tilting member being disposed on a substrate and inclining the corresponding illuminating unit so that the emitting surface of the illuminating unit is inclined in an outward direction from the optical axis of the image capturing unit.

10. The capsule endoscope according to claim 9, wherein the illuminating units have a light distribution characteristic that uniformly illuminates the vision range of the image capturing unit.

11. The capsule endoscope according to claim 10, wherein illuminating ranges of the illuminating units overlap so that the vision range of the image capturing unit is uniformly illuminated.

* * * * *